United States Patent [19]

Harris et al.

[11] 3,930,812
[45] Jan. 6, 1976

[54] METHANE SYNTHESIS

[75] Inventors: Norman Harris, Stockton-on-Tees; Ray Fowler, Amersham, both of England

[73] Assignee: Davy Powergas Limited, London, England

[22] Filed: June 24, 1974

[21] Appl. No.: 482,254

[30] Foreign Application Priority Data
July 13, 1973 United Kingdom............... 33427/73

[52] U.S. Cl. .......................... 48/197 R; 260/449 M
[51] Int. Cl.² ........................................... C10K 3/02
[58] Field of Search ............... 48/197 R; 260/449 M

[56] References Cited
UNITED STATES PATENTS
3,511,624  5/1970  Hamphries et al. ............ 260/449 M

*Primary Examiner*—S. Leon Bashore
*Assistant Examiner*—George C. Yeung
*Attorney, Agent, or Firm*—Morton, Bernard, Brown, Roberts & Sutherland

[57] ABSTRACT

A process is provided for the catalytic production of methane from carbon oxides and hydrogen wherein water is introduced into the reaction vessel for the removal of the heat of reaction by the production of steam with the use of a catalyst effective at a temperature below 500°F. The catalyst is a Group 8 metal, preferably mixtures of nickel and metals of the platinum group. Feedstock gas is normally obtained by gasification of fossil fuels or aliphatic alcohols with steam and/or oxygen.

17 Claims, 1 Drawing Figure

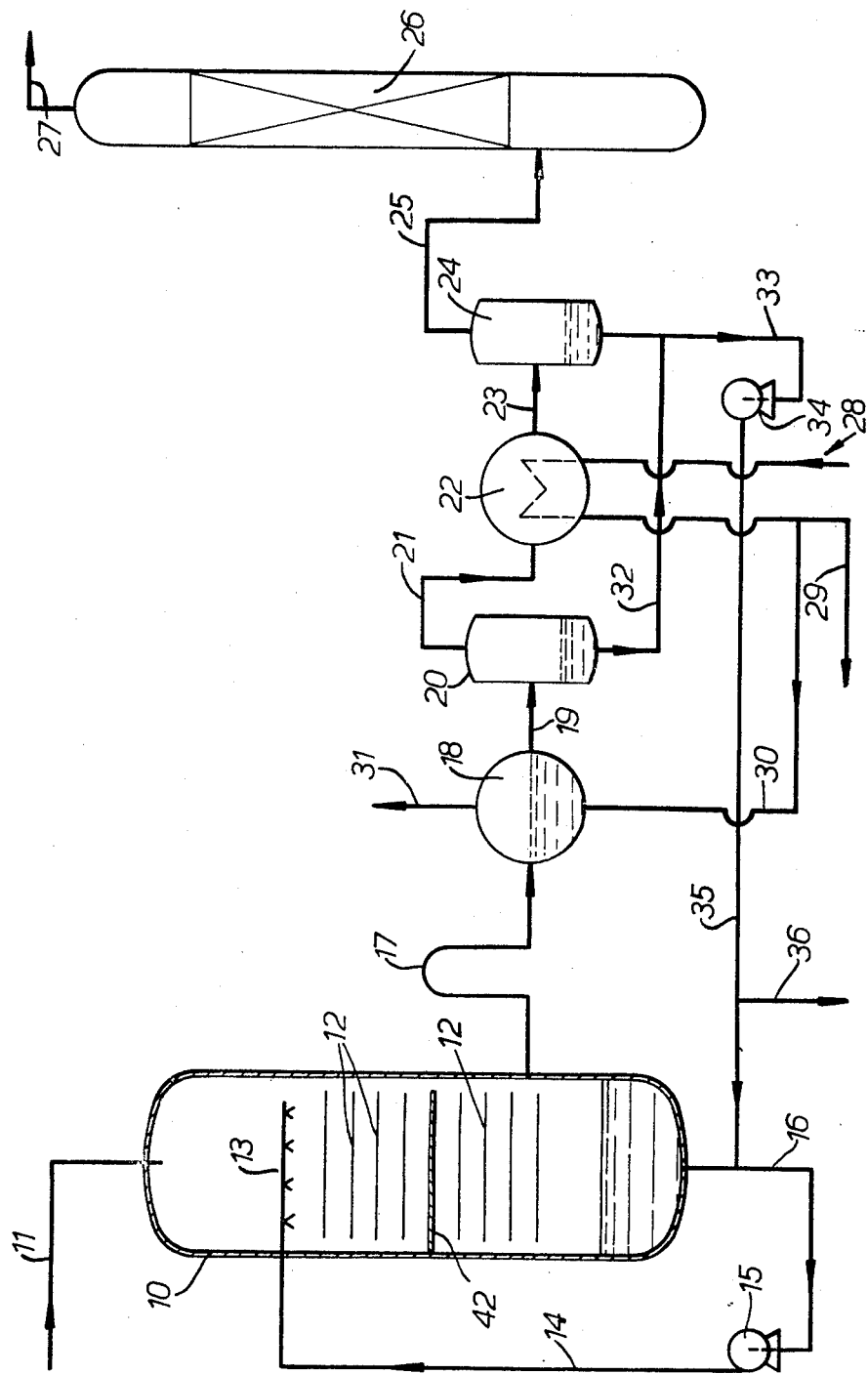

METHANE SYNTHESIS

This invention relates to a process for the production of methane by reaction of hydrogen with carbon monoxide and/or carbon dioxide and to catalysts to be used therein.

The synthesis of methane from carbon oxides is well known for the purification of gases containing small proportions of carbon monoxide and carbon dioxide. It is now of increasing interest and importance as a means of producing synthetic natural gas.

The methanation process is normally envisaged as the reaction of carbon monoxide with hydrogen according to the following equation $$Co + 3H_2 \rightarrow CH_4 + H_2O$$

In the production of synthetic natural gas from fossil fuels, a gas containing hydrogen and carbon oxides is first produced. It is then normal practice to react these gases with steam in order to produce more hydrogen by reaction with carbon monoxide, known as shift conversion, according to the following equation $$Co + H_2O \rightarrow CO_2 + H_2$$

This shift conversion is carried out to the extent that the final gas has a carbon monoxide:hydrogen ratio of 1:3. The carbon dioxide produced may be removed either before or after the methanation of carbon monoxide with hydrogen.

According to the present invention there is provided a process for the production of methane by the reaction of hydrogen with carbon monoxide and/or carbon dioxide in the presence of water for the removal of the heat of reaction and with the use of a catalyst which is effective at a temperature below 500°F.

In the practice of the present invention it is not essential to carry out a shift conversion reaction in the preparation of an initial feed gas mixture because both carbon monoxide and carbon dioxide are reacted with hydrogen to produce methane, and the product gas composition approaches equilibrium for the following three reactions simultaneously $$CO + 3H_2 \rightarrow CH_4 + H_2O$$
$$CO_2 + 4H_2 \rightarrow CH_4 + 2H_2O$$
$$CO + H_2O \rightarrow CO_2 + H_2$$

This fact, however, does not represent the main benefit secured by the present invention the major advantage of which resides in the removal of the heat of reaction. In all methane synthesis processes, a major problem lies in the question of removal of exothermic heat of reaction. The exothermic methanation reactions of both carbon monoxide and carbon dioxide have heats of reaction ($\Delta H_{25}°$ $_c$) of −49.27 and −39.44 kcal/mole of carbon oxide respectively. The theoretical temperature rise therefore for a typical methanator gas composition is 74°C per 1% of carbon monoxide converted and 60°C per 1% of carbon dioxide converted. Techniques proposed to overcome this heat removal problem have included, either alone or in combination, 1. The re-cycling of very large quantities of product gas in order to reduce the concentration of carbon oxide and limit the temperature rise. In this way the heat is removed from the system in the recycled gas.
2. The amount of methanation in any single reactor can be limited by the conditions of temperature, pressure and steam content so producing a safe temperature rise, and this technique is employed in multi-stage reactors with heat removal between stages.
3. Proposals have also been made to remove the heat of reaction through the wall of a tube or tubes, in which the catalyst is placed. This may be employed in either a fixed catalyst bed or a fluid bed.

The present invention does not employ any of the above mentioned techniques, but involves the use of a trickle type of reactor into which water is introduced in the liquid phase. As the gas and water pass over a catalyst and methanation takes place, the temperature rise is controlled by the evaporation of part of the water. The water may be introduced as a spray over the catalyst, and the flows of gas and water over the bed of the catalyst may be co-current. The spray may be introduced at one or more places in the reaction chamber.

This technique has not been considered possible in the past because the steam produced has an unfavourable effect on the methanation reaction equilibra. The technique however, becomes possible with the use of catalysts which are able to function at temperatures below 500°F and which we have now found. At these temperatures the equilibrium under most normal conditions, favours methane production to an extent which permits the presence of large excesses of steam. The use of this lower temperature also permits some of the water to remain in the liquid phase at most operating pressures and temperatures. The reactor and the process are intrinsically safe because it is impossible in the presence of liquid water for the catalyst to become overheated. The reaction is near to isothermal conditions.

The catalyst employed is conveniently a Group 8 metal. Catalysts particularly suitable for the present methanation process include those containing raney nickel and metals of the platinum group. Binary mixtures of nickel and/or platinum group metals have also been found to be effective.

A number of variations are possible. The water and synthesis gases may, for example, pass over the catalyst counter-current to each other. This however suffers from the disadvantage that there may be a danger of flooding as water is held up in the reactor due to high gas rates, and co-current operation is accordingly preferred.

The process itself may be operated at pressures between 0 and 2000 psig, preferably super-atmospheric pressure, most preferably from 250 to 350 psig, and is preferably operated at a temperature below 550°F, most preferably from 350° to 400°F.

The methanation may be completed in two or more stages. With such operation it may be possible for only one of the stages to incorporate the principle of an aqueous trickle reaction. With a multi-stage system, water or carbon dioxide may be removed between stages. Preferably carbon dioxide is removed from the off-take after separation of water.

It is not normally necessary to shift convert the synthesis gas used as feedstock in order to produce a 3:1 hydrogen carbon monoxide ratio. This however is optional and the present process can readily accept such a process gas.

The feedstock for the process will, however, normally be procduced by the gasification of fossil fuels or aliphatic alcohols with steam and/or oxygen. For example, methanol may be reacted with steam over an iron oxide/chromium oxide catalyst to provide a feedstock for further methanation. Methanation will also normally be followed by removal of carbon dioxide from the gaseous reaction product.

The heat of reaction is normally recovered after the methanation by cooling and condensing the major portion of the steam present in the product gases. This heat can be used to generate steam or to pre-heat boiler feed water. It is not normally possible to raise steam at a sufficiently high pressure to pass to a gasification stage preceding the methanation step. This is however true if the gas, after production and purification, has been compressed into the methanator. It may also be desirable to provide a reactor having a number of reaction beds with re-distribution between them of water collected at intervals along the reactor. It is also possible, and some times desirable to inject water at various points in the reactor. Water is in any case recovered after use in the reaction and is recycled.

The accompanying drawing represents schematically and not to scale a plant for carrying out a process in accordance with the invention.

In the drawing a main reaction vessel or methanator is represented at 10 and is fed at its upper end with gas from a LURGI coal gasification plant having a composition CO, 25.0%; $CO_2$, 25.0%; $CH_4$, 10.0%; $H_2$, 35.0%; $N_2$, 2.5%. The gas is fed at a temperature of 363°F at 310 psig at the rate of 7,350,000 NCFH by the inlet line 11 to the reactor 10 having supports 12 for catalyst and water inlets 13 fed by line 14 from the pump 15. A water re-distributor is indicated at 42. The specific gravity of the feedstock gas supplied to the reactor is 0.32 relative to air. Water collected at the base of the reactor is recycled by pump 15 from pipeline 16 while reaction product gas is taken by off-take line 17 to a low pressure steam boiler 18. The product gas has a composition of CO, 0.1% v/v; $CO_2$, 55.0%; $CH_4$, 40.8%; $H_2$, 0.9%; and $N_2$, 3.2%. The specific gravity is 2.02, temperature 382°F and pressure 300 psig. Off-take is at the rate of 4,600,000 NCFH. Water supplied to the reactor is about 350,000 lbs per hour and the catalyst is a Raney nickel catalyst containing metals of the platinum group.

The product gas leaves steam generator 18 by the line 19 at 293 psig and a temperature of 330°F and passes to a water separator 20 emerging by line 21 with a specific gravity of 0.356. The line 21 leads to a feed water heater 22 and the exit 23 therefrom passes to a further water separator 24. Off-take line 25 from the second water separator leads to the $CO_2$ removal tower 26. Gas in line 25 is at a temperature of 190°F and pressure of 288 psig. The product gas from the $CO_2$ remover (exit shown at 27) has a composition of CO, 0.1% v/v; $CO_2$, 0.1%; $CH_4$, 90.6%; $H_2$, 2.1%; and $N_2$, 7.1%; and is delivered at a rate of 2,080,000 NCFH.

The boiler feed water heater 22 is fed with water at 100°F through the line 28 at a rate of 578,000 lbs per hour and off-take through the line 29 at 290°F supplies 204,000 lbs per hour feed water for other boilers and the remainder through line 30 to the low pressure boiler 18 which delivers 374,000 lbs per hour of steam at 50 psig.

The first water separator 20 supplies 373,200 lbs per hour of water to the off-take line 32 to which is added 78,490 lbs per hour of water from the second water separator 24 in the line 33 leading to pump 34 which returns water by the line 35 to the line 16 for recirculation by pump 15. Line 36 is an off-take for excess water amounting to 114,190 lbs per hour.

It is claimed:

1. A process for the production of methane comprising reacting hydrogen and at least one carbon oxide selected from the group consisting of carbon monoxide and carbon dioxide, said hydrogen and carbon oxide comprising a gas, by passing said gas over a Group VIII metal-containing catalyst, which catalyst is effective for the reaction at a temperature below 500°F., at a temperature sufficient to vaporize water and below 550°F. and at a pressure of 0 to 2000 psig. in the presence of water in the liquid phase to form methane and to vaporize water to remove the heat of the reaction.

2. A process for producing a product gas containing increased methane by the reaction of hydrogen with carbon monoxide and/or carbon dioxide comprising feeding a gaseous feedstock produced by gasification of fossil fuels or aliphatic alcohols with steam and/or oxygen to a reaction chamber which contains a catalyst of a Group VIII metal and is effective for the reaction at a temperature below 500°F., spraying water in the liquid phase over the catalyst so that the water evaporates and removes the heat of reaction within the chamber, the reaction in the chamber being carried out below a temperature of 550°F. and at a pressure of 0 to 2000 psig, to form the product gas of increased methane content.

3. A process for the production of methane comprising reacting hydrogen with carbon monoxide or carbon dioxide in the presence of water in the liquid phase, removing the heat of reaction by evaporation of the water, said reaction being conducted with the use of a catalyst which is effective for the reaction at a temperature below 500°F.

4. The process of claim 17 wherein the reaction temperature is below 550°F.

5. The process of claim 3 wherein the reaction is carried out at a super-atmospheric pressure up to 2000 psig.

6. The process of claim 3 wherein the reaction is carried out at a temperature of from 350° to 400°F. and at a pressure of from 250 psig to 350 psig.

7. The process of claim 3 wherein the hydrogen and carbon monoxide or carbon dioxide are produced by gasification of fossil fuels or aliphatic alcohols with steam and/or oxygen.

8. The process of claim 7 wherein the gasification product is subjected to a shift conversion reaction prior to methanation.

9. The process of claim 3 in which liquid water is introduced into a reaction chamber which contains the catalyst for methanation.

10. The process of claim 9 wherein the liquid water is recycled through the reaction chamber.

11. The process of claim 9 wherein off-take from the methanation contains carbon dioxide and water, and carbon dioxide is removed from the off-take after separation of water.

12. The process of claim 11 wherein the off-take from the reaction chamber and water separation are effected with recovery of heat from the off-take.

13. The process of claim 3 wherein the water is present as a spray over the catalyst and the gas and liquid water flows are co-current.

14. The process of claim 9 wherein the water is present as a spray and is introduced at at least one place in the reaction chamber over the catalyst and the gas and water flows are co-current.

15. The process of claim 3 wherein the methanation is effected in at least two stages.

16. The process of claim 3 wherein the catalyst comprises a Group VIII metal.

17. The process of claim 16 wherein the catalyst comprises Raney nickel and at least one metal of the platinum group.

* * * * *

UNITED STATES PATENT AND TRADEMARK OFFICE
CERTIFICATE OF CORRECTION

PATENT NO. : 3,930,812
DATED : January 6, 1976
INVENTOR(S) : NORMAN HARRIS and RAY FOWLER It is certified that error appears in the above-identified patent and that said Letters Patent are hereby corrected as shown below:

Column 1, line 16, the equation should appear -- CO --

Column 1, line 23, the equation should appear -- CO --

Column 1, line 51, the figures in the parentheses should appear -- ($\Delta H_{25°C}$) --

Column 2, line 62, correct the spelling of "produced"

Column 4, line 29, "17" should be -- 3 --.

Signed and Sealed this fifteenth Day of June 1976

[SEAL]

Attest:

RUTH C. MASON
Attesting Officer

C. MARSHALL DANN
Commissioner of Patents and Trademarks